US008735822B2

(12) United States Patent
Thomson et al.

(10) Patent No.: US 8,735,822 B2
(45) Date of Patent: May 27, 2014

(54) METHOD FOR DETECTING AND MEASURING LOW CONCENTRATIONS OF CONTAMINANTS USING ATTENUATED TOTAL REFLECTANCE SPECTROSCOPY IN THE MID-IR RANGE

(75) Inventors: Mary Thomson, Sturbridge, MA (US); Peter Melling, Sturbridge, MA (US)

(73) Assignee: Remspec Corporation, Sturbridge, MA (US)

( * ) Notice: Subject to any disclaimer, the term of this patent is extended or adjusted under 35 U.S.C. 154(b) by 71 days.

(21) Appl. No.: 13/208,674

(22) Filed: Aug. 12, 2011

(65) Prior Publication Data

US 2013/0037719 A1 Feb. 14, 2013

(51) Int. Cl.
*G01N 21/35* (2014.01)
(52) U.S. Cl.
USPC .......................................... 250/340

(58) Field of Classification Search
USPC .......................................... 250/340
See application file for complete search history.

(56) References Cited

U.S. PATENT DOCUMENTS

| 5,097,129 | A | * | 3/1992 | de Vries et al. | 250/338.1 |
| 2006/0043301 | A1 | * | 3/2006 | Mantele et al. | 250/339.11 |
| 2012/0170023 | A1 | * | 7/2012 | Szobota et al. | 356/51 |

* cited by examiner

*Primary Examiner* — David Porta
*Assistant Examiner* — Hugh H Maupin

(57) ABSTRACT

A spectroscopic method is disclosed for detecting and measuring contaminants in fluids such as water or oil, where the hydrophilicity of the contaminant is substantially different from that of the contaminated fluid. Good calibrations can be obtained at very low concentrations using infrared spectroscopy with ATR crystals that have not been additionally coated or otherwise modified.

16 Claims, 5 Drawing Sheets

*Infrared Element (IRE), showing mechanism of attenuated total reflectance (ATR) effect.*

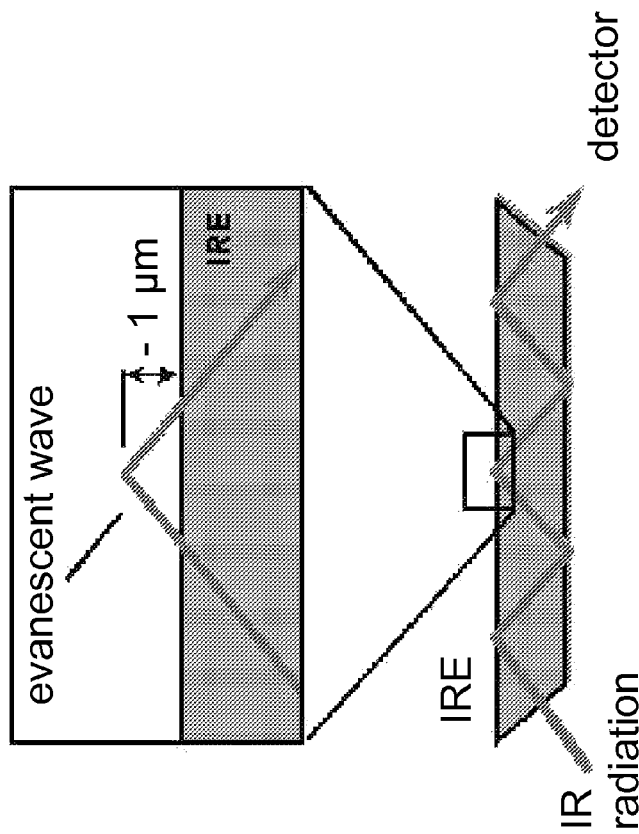
Figure 1: Infrared Element (IRE), showing mechanism of attenuated total reflectance (ATR) effect.

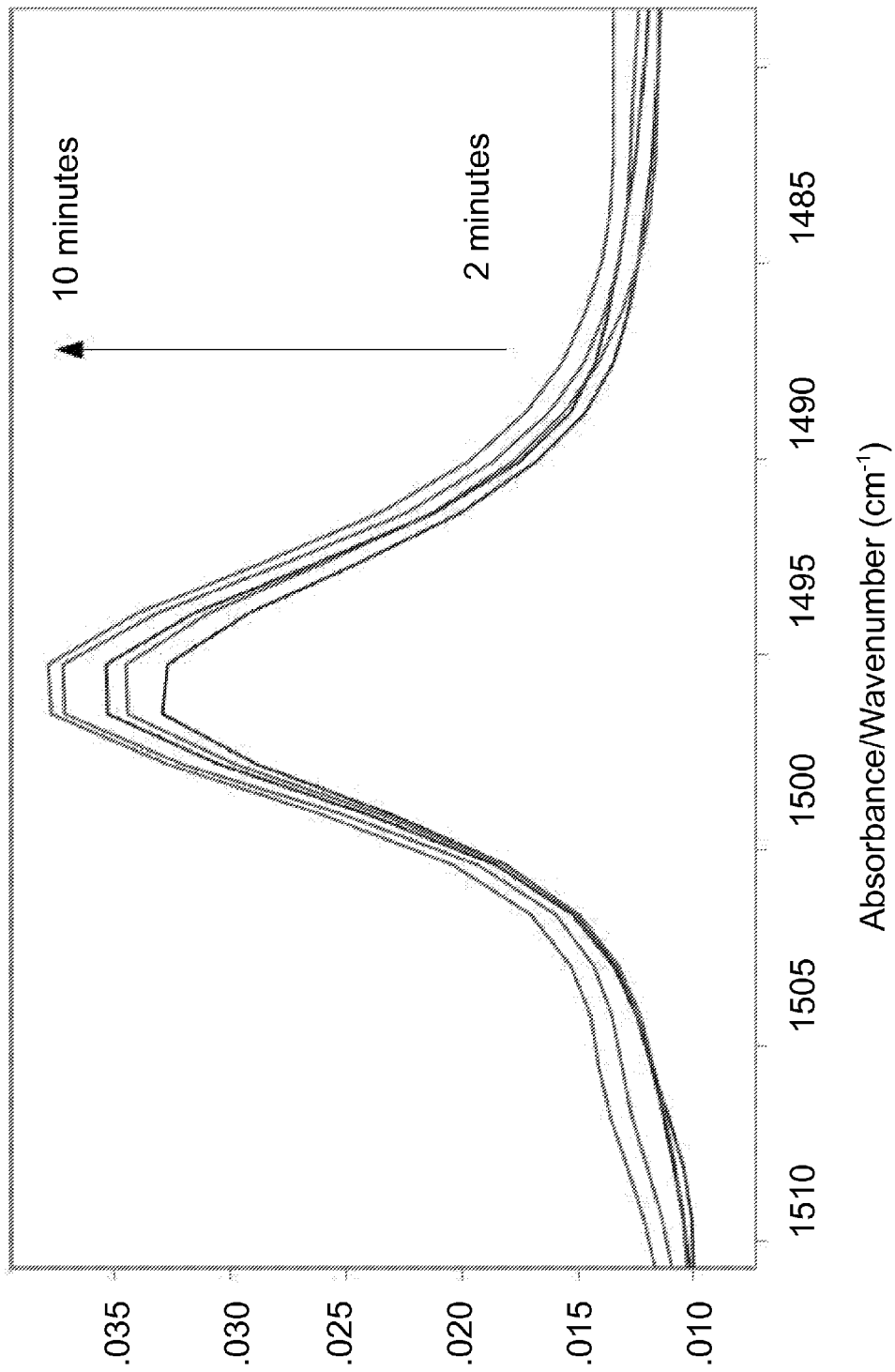
Figure 2: Selected peak from FTIR spectrum of 200 ppm (by volume) toluene in water, obtained using a flat ATR crystal coated with approx. 10 μm ethylene-propylene copolymer.

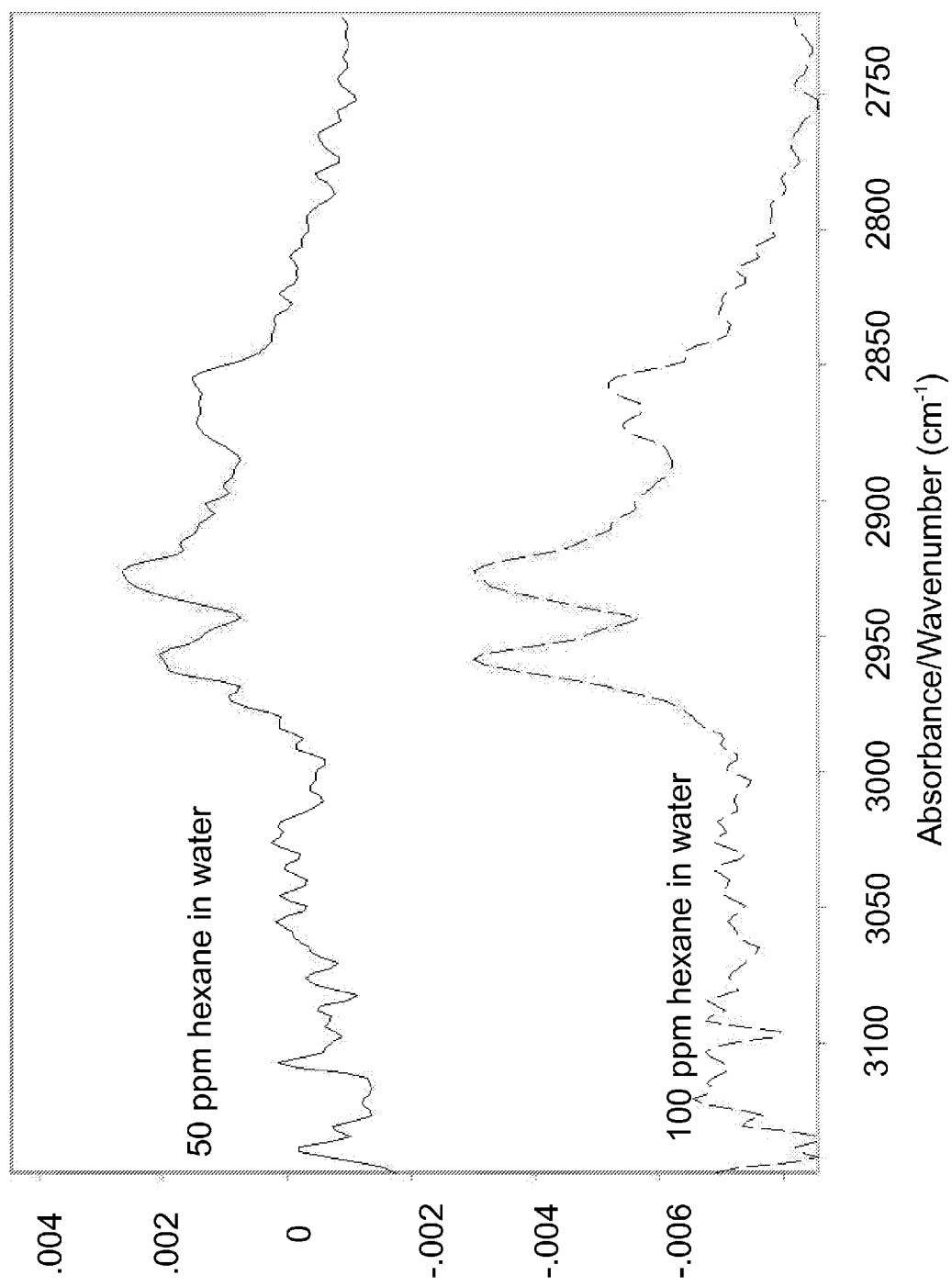
Figure 3: FTIR ATR spectra of 50 and 100 ppm hexane in water, using ZnS ATR crystal

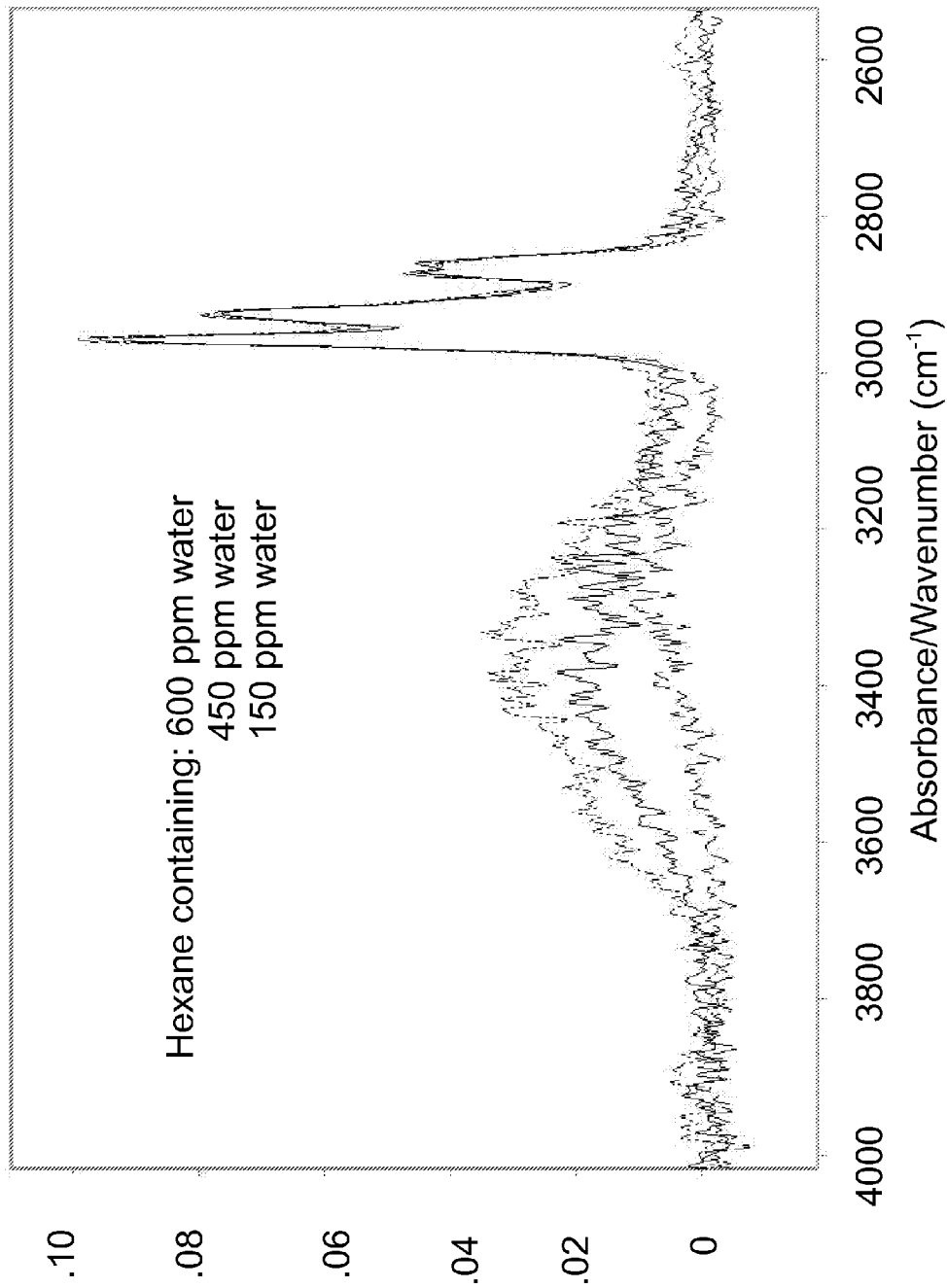
Figure 4: FTIR ATR spectra of 150, 450, and 600 ppm water in hexane, using Ge ATR crystal

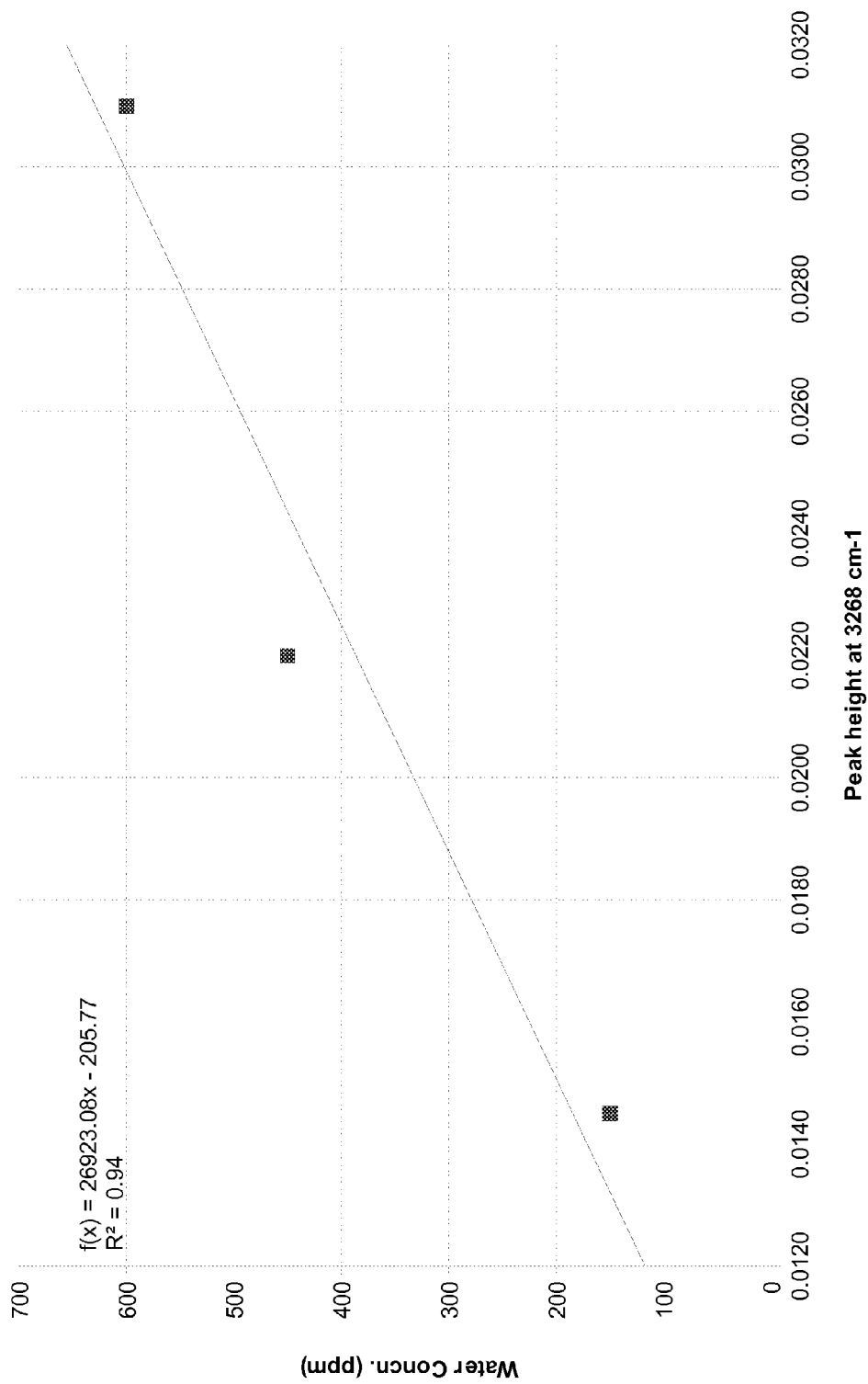
Figure 5: Graph of water concentration in ppm versus peak height at 3268 cm$^{-1}$

METHOD FOR DETECTING AND MEASURING LOW CONCENTRATIONS OF CONTAMINANTS USING ATTENUATED TOTAL REFLECTANCE SPECTROSCOPY IN THE MID-IR RANGE

BACKGROUND OF THE INVENTION

1. Field of the Invention

The present invention relates to the use of spectroscopic methods to detect and measure very low levels of contaminants in water, oils, and other media.

2. Background of the Invention

Contamination of water, including drinking water, ground water, and seawater, poses considerable problems for human health and for the environment. Certain industrial processes also require water that is free from organic materials at the level of parts per million (ppm) or parts per billion (ppb). For different reasons, it can be important to detect small quantities of water in organic matrices such as crude oil, kerosene, lubricating oil, or gasoline.

A range of analytical procedures for the determination of hydrocarbons in water is available in the literature. A number of ISO standards have been published that specify methods for measuring organic contaminants in water (see Table 1).

TABLE 1

Examples of ISO standards for organic contaminant analysis in water

| Standard Number | Target | Method |
| --- | --- | --- |
| ISO 10301: 1997 | Highly volatile halogenated hydrocarbons | Gas chromatographic (GC) methods |
| ISO 10695: 2000 | Selected organic nitrogen and phosphorus compounds | GC methods |
| ISO 11423-2: 1997 | Benzene and some derivatives | Extraction and GC |
| ISO 15680: 2003 | A number of monocyclic aromatic hydrocarbons, naphthalene and several chlorinated compounds | GC determination using purge-and-trap and thermal desorption |
| ISO 17495: 2001 | Selected nitrophenols | Solid-phase extraction and gas chromatography with mass spectrometric detection (GC/MS) |
| ISO 17858: 2007 | Polychlorinated biphenyls | GC/MS |
| ISO 17993: 2002 | 15 polycyclic aromatic hydrocarbons (PAH) | High-Performance Liquid Chromatography (HPLC) with fluorescence detection after liquid-liquid extraction |
| ISO 18857-1: 2005 | Selected alkylphenols | Method for non-filtered samples using liquid-liquid extraction and GC/MS |
| ISO 6468: 1996 | Certain organochlorine insecticides, polychlorinated biphenyls and chlorobenzenes | GC method after liquid-liquid extraction |
| ISO 7981-2: 2005 | PAH | HPLC with fluorescence detection after liquid-liquid extraction |
| ISO 8165-1: 1992 | Selected monovalent phenols | GC method after enrichment by extraction |
| ISO 8165-2: 1999 | Selected monovalent phenols | Derivatization and GC |
| ISO 9377-2: 2000 | Determination of hydrocarbon oil index | Solvent extraction and GC |

All of the listed ISO methods include at least an extraction/concentration step, or a purge-and-trap step; some include a derivatization step. All are essentially laboratory-based methods, unsuitable for implementation in the field, or for continuous monitoring of process or waste fluids.

The determination of water content in hydrocarbon streams such as crude oil, fuel oil, or mineral oil is also of considerable economic importance. The presence of even quite small amounts of water can interfere with the processing of crude oil, and can compromise the performance of fuel oil. Water in machine or engine oil can lead to accelerated wear or corrosion of machine or engine parts. Consequently, a range of standard methods exist for the determination of water content in oil (see Table 2).

TABLE 2

Examples of standards for water determination in oil

| Standard Number | Target | Method |
| --- | --- | --- |
| ASTM D4006 - 07 (ISO 9029) | Standard Test Method for Water in Crude Oil by Distillation | Distillation |
| ASTM D95 | Test Method for Water in Petroleum Products and Bituminous Materials by Distillation | Distillation |
| ASTM D96 | Test Methods for Water and Sediment in Crude Oil by Centrifuge Method (Field Procedure) | Centrifugation |

In general, the standard methods are based on distillation, which is a complex method and not suitable for field or process use, or on centrifugation.

A Fourier-transform infrared (FTIR) spectroscopic method for analyzing organics in water has the potential to be a fast, non-complex technique, offering the elimination of the extraction/concentration step, the purge-and-trap step, or the derivatization step. However, existing procedures for IR analysis of organics in water generally include an extraction step (see, for example Application Note: *Determination of Oil and Grease in Water with a Mid-Infrared Spectrometer*, PerkinElmer Inc., 2009). While a number of small, portable instruments are available that lend themselves to field use, they too require an extraction step (see, for example Application Note: *New ASTM Test Method Offers Quick and Easy Oil and Grease*, Sandra Rintoul, Wilks Enterprise Inc.) The extraction step is carried out because (a) water absorbs very strongly in the mid-IR, making transmission measurements impossible and (b) the ATR method has not generally been considered sensitive enough to detect parts per million of organics in water.

FIG. 1 illustrates the mechanism of the attenuated total reflectance (ATR) effect in an infrared element (IRE) such as a zinc selenide, zinc sulfide, or diamond crystal. When the IRE is immersed in a fluid sample, the evanescent wave penetrates into the sample to a depth determined by the ATR equation:

$$d_p = \frac{\lambda}{2\pi n_p (\sin^2\theta - n_{sp}^2)^{1/2}}$$

where $d_p$ is the penetration depth at each bounce
$\lambda$ is the wavelength of the radiation
$n_p$ is the refractive index of the crystal
$\theta$ is the angle of incidence of the light beam
$n_{sp}$ is the ratio of the refractive indices of sample and crystal Based on this equation, the signal penetration depth into water, using any of the conventional ATR materials, is in the range of a few micrometers. While this enables the use of mid-IR spectroscopy in high-absorbing media such as water by decreasing the path length dramatically versus transmission methods, it limits the sensitivity of the technique. Typically, an ATR measurement is expected to be at least an order of magnitude less sensitive than a comparable transmission measurement, even at the lowest obtainable transmission path lengths. Considerable effort has been made to develop a method that combines the desirable attributes of ATR-FTIR methods (rapid, direct, reproducible measurement, effective in water) with the sensitivity of extraction methods or transmission-FTIR.

Efforts to eliminate a separate extraction step, or other concentration step, have included the use of so-called molecular enrichment layers, or solid-phase micro-extraction layers (SPME layers), on ATR crystals. These layers are applied to the surface of the ATR element so as to selectively concentrate the target analyte close to the crystal surface and within the region that is sampled by the evanescent wave during the ATR measurement. Much of the published work in this area has involved thin polymeric coatings on zinc selenide or zinc sulfide ATR crystals (see, for example, *"Amplified" Fiber-Optic ATR Probes with Improved Detection Limits in the Mid IR*, presented at the Federation of Analytical Chemistry and Spectroscopy Societies (FACSS) Meeting in Providence, R.I., 2002, by P. Melling, M. Thomson, B. Mizaikoff, and M. Karlowatz; *From the Lab to the Field—Recent Developments in Polymer Coated ATR*, thesis by M. Karlowatz, Georgia Institute of Technology, 2004; *Development of an SPME/ATR-IR chemical sensor for detection of phenol type compounds in aqueous solutions*, J. Yang and M-L Cheng, *The Analyst*, 2001, 126, 881-886). These layers, typically comprising hydrophobic polymers such as ethylene-propylene copolymer or PTFE, have the effect of selectively concentrating hydrophobic analytes close to the ATR surface and thus enhancing the resulting FTIR signal. While this method has proven to be very sensitive, it is difficult to calibrate and the robustness of the coated ATR elements has not been demonstrated. Coatings made from oxide nanoparticles, from zeolites, and sol-gel silica have also been used as SPME layers to promote ATR detection of organics in water.

A related, but different, approach involves combining an ATR crystal with a membrane-based micro liquid-liquid extraction cell to create a sensor which performs a micro-extraction of organics from an aqueous stream to deliver a concentrated sample to the ATR element (M. Vacarcel et al., *ATR-FTIR membrane-based sensor for the simultaneous determination of surfactant and oil total indices in industrial degreasing baths, Analyst*, 2006, 131, pp. 415-421). Like the SPME layers, this method has the potential to be very sensitive. However, it is essentially a laboratory-based approach which would be difficult to implement in the field. Furthermore, as described by Valcarcel, it involves the use of environmentally unacceptable solvents such as carbon tetrachloride.

Water content in oils, e.g. in industrial lubricants, is also an important measurement, and presents a similar challenge. Many currently accepted standard methods, such as Karl Fischer Titration, for example, are laboratory-based. An FTIR method is described in ASTM E2412-10 *Standard Practice for Condition Monitoring of Used Lubricants by Trend Analysis Using Fourier Transform Infrared (FT-IR) Spectrometry*, and an improved method using FTIR has been proposed recently (US Patent Application 2009/0257047 by Higgins and Seelenbinder, and Application Note 101: *On-Site, Low Level Quantitative FTIR Analysis of Water in Oil Using a Novel Water Stabilization Technique*, by Higgins and Seelenbinder, A2 Technologies). The method of Higgins and Seelenbinder involved treating the oil sample with a surfactant to stabilize and evenly distribute the water content before measuring a transmission spectrum and using a suitable univariate or multivariate calibration to determine the water content.

All of the FTIR methods described for both oil-in-water and water-in-oil analysis involve specific steps to concentrate the analyte, or stabilize its distribution throughout the sample, before carrying out the FTIR analysis. In the ATR measurement, which is the only practical method for measuring FTIR spectra in aqueous samples due to the very high IR absorption of water, the development of a suitable process to concentrate the analyte has been extensively studied. The concentration is carried out either as a separate step, resulting in a sample where the analyte is concentrated, or by treating a conventional ATR material, such as zinc selenide, zinc sulfide, or diamond, with specialized coatings which enhance the analyte concentration near the ATR surface, so as to facilitate analysis down to the level of parts per million (ppm).

In light of the extensive literature describing pre-concentration or stabilization of the analyte, and pretreatment of ATR crystals to enhance analyte detection by surface concentration, the present discovery that certain ATR materials are sufficiently hydrophobic to promote analyte enrichment close to the ATR surface, and thus to enable detection of organics in water down to ppm levels, is completely contrary to expectations. Similarly, the ability of more hydrophilic ATR materials to enable detection of ppm water in organic media such as oil is surprising.

SUMMARY OF THE INVENTION

It is an object of the present invention to provide a means for detecting and measuring low concentrations of contaminants in aqueous and non-aqueous fluids by a spectroscopic method using standard ATR materials, without pretreatment or extraction of the analyte and without surface modification of the ATR element.

BRIEF DESCRIPTION OF THE DRAWINGS

FIG. 1 is a schematic drawing illustrating the mechanism of the ATR effect

FIG. 2 shows FTIR spectra of water, and water containing 200 ppm toluene, taken using a coated ATR crystal (prior art)

FIG. 3 shows FTIR ATR spectra of 100 ppm hexane in water, obtained using the uncoated ZnS ATR crystal FIG. 4 shows the FTIR ATR spectra of 150, 450, and 600 ppm water in hexane, using a germanium ATR crystal FIG. 5 is a graph of water concentration versus peak height for water in hexane

DETAILED DESCRIPTION OF THE PREFERRED EMBODIMENTS

In one preferred embodiment, an ATR crystal made of optical-grade zinc sulfide, which is hydrophobic, is attached to the end of a spectroscopic probe comprising infrared-transmitting optical fibers. This type of probe is described in U.S. Pat. No. 5,170,056, which is included here by reference. In this preferred embodiment, the ATR crystal is attached to the end of the fiber-optic probe by means of a direct coupling between the optically flat end of the probe (comprising a polished bundle of infrared-transmitting optical fibers) and the optically flat proximal end of the crystal. The distal end of the ATR crystal is typically a cone (giving a 2-bounce ATR element) or a truncated cone (giving a 3-bounce ATR element).

When the crystal is exposed to a liquid sample, such as water, containing a low level of contamination, such as ppm levels of a hydrocarbon oil, the hydrophobic surface of the ATR crystal interacts with the sample so as to minimize the concentration of water molecules in the layer that directly contacts the crystal surface, and thus to maximize the concentration of organic molecules. This has the effect of concentrating the organic material in the approximately 1-micrometer thick layer that is sampled by the evanescent wave from the ATR crystal (see FIG. 1). The concentration of organic material close to the ATR surface has the effect of amplifying the detection of low levels of organic contamination in the aqueous fluid. As a result concentration below 100 ppm can be measured for some hydrocarbons, as described in Example 2.

A second preferred embodiment of the invention is of utility in the case where a very low concentration of water is required to be measured in a fluid organic medium such as a hydrocarbon oil. When an ATR crystal made of a relatively hydrophilic material, e.g. zirconia or germanium, is exposed to an organic sample such as an engine cooling oil, the surface of the crystal interacts with the sample so as to maximize the concentration of water in the layer that directly contacts the crystal surface, with the effect of amplifying the FTIR signal that is measured for the water, and thus enhancing the detection of low levels of water in the organic medium.

The following examples illustrate a prior-art method and preferred embodiments of the invention:

Procedure:

FTIR/ATR spectra were collected using a Remspec ReactionView® system comprising a compact mid-IR FTIR unit, a liquid nitrogen-cooled MCT detector, and a fiber-optic probe equipped with interchangeable ATR analysis heads. Bruker Optics OPUS software was used for data acquisition.

A background spectrum was acquired by immersing the ATR head in the appropriate fluid (distilled water or ambient air). The sample spectra were collected by immersing the ATR crystal in the sample solution, and acquiring data for 1 minute at a resolution of 4 $cm^{-1}$. Care was taken to clean and dry the ATR crystal thoroughly between samples.

EXAMPLE 1

Prior Art

A solution of toluene in water (200 ppm) in distilled water was prepared and its FTIR spectrum (distilled water background) was collected using a ZnS ATR crystal with a coating of ethylene-propylene copolymer (approx. 10 micrometers thick, applied by dip-coating). Spectra were collected every minute for 10 minutes. The prominent peak near 1495 $cm^{-1}$, usually assigned to the aromatic C-C stretch, is shown in FIG. 2 after data collection for 2, 4, 6, 8, and 10 minutes. The intensity of the peak increases over time as toluene is concentrated in the polymer layer close to the surface of the ATR element. This complicates calibration of the method, and makes real-time data collection difficult.

EXAMPLE 2

Two solutions of hexane (50 and 100 ppm by weight) in distilled water were prepared and their FTIR spectra (distilled water background) were collected using a ZnS ATR crystal attached to the fiber-optic probe. A feature was observed between 2800 and 3000 $cm^{-1}$ (see FIG. 3); this is characteristic of the C-H stretch of hydrocarbon compounds; the feature varies in proportion to the hexane concentration.

EXAMPLE 3

Three solutions of water in hexane were prepared (600, 450, and 150 ppm by weight) and the FTIR spectra (air background) were collected using a germanium ATR crystal attached to the fiber-optic probe. A feature was observed between 3130 and 3690 $cm^{-1}$ (see FIG. 4); this is characteristic of the O—H stretch of water. A simple graph of peak height versus water concentration (FIG. 5) shows that the relationship is quantitative, and that quantitative calibration is possible.

While the above description contains many specific details and descriptions, these should not be taken as limiting the scope of the invention, but rather as exemplifications of preferred embodiments. Many other variations are possible, and will be apparent to those skilled in the art. The scope of the invention should be determined not by the embodiments illustrated, but by the appended claims and their legal equivalents.

What is claimed is:

1. An IR spectroscopic method for detecting the presence, and measuring the amount, of one or more contaminants in a fluid, the method comprising: exposing an ATR element to the fluid, and characterized in that:
   the contaminant and the fluid are of substantially different hydrophilicity,
   the ATR element is composed of a material selected so as to have a hydrophilicity which is more closely similar to that of the contaminant than it is to that of the fluid,
   the ATR element is composed of an ATR material having no additional coating or surface treatment.

2. The method of claim 1, wherein the ATR material is selected from zinc sulfide, zinc selenide, diamond, a chalcogenide glass, cadmium sulfide, cadmium telluride, gallium arsenide, KRS5, silicon, germanium, or zirconium oxide.

3. The method of claim 1, wherein the contaminant is a organic compound and the fluid is water or an aqueous solution or mixture.

4. The method of claim 3, wherein the organic compound is a hydrocarbon.

5. The method of claim 3, wherein the contaminant is a chlorinated hydrocarbon.

6. The method of claim 3, wherein the contaminant is an oxygenated hydrocarbon.

7. The method of claim 3, wherein the ATR material is zinc sulfide or diamond.

8. The method of claim 4, wherein the ATR material is zinc sulfide or diamond.

9. The method of claim 5, wherein the ATR material is zinc sulfide or diamond.

10. The method of claim 6, wherein the ATR material is zinc sulfide or diamond.

11. The method of claim 1, wherein the contaminant is water and the fluid is a hydrocarbon.

12. The method of claim 1, wherein the contaminant is water and the fluid is a chlorinated hydrocarbon.

13. The method of claim 1, wherein the contaminant is water and the fluid is an oxygenated hydrocarbon.

14. The method of claim 11, wherein the ATR material is germanium or zirconium oxide.

15. The method of claim 12, wherein the ATR material is germanium or zirconium oxide.

16. The method of claim 13, wherein the ATR material is germanium or zirconium oxide.

* * * * *